United States Patent
Cohen et al.

(10) Patent No.: US 7,003,072 B2
(45) Date of Patent: Feb. 21, 2006

(54) METHOD FOR LOCALIZING A TARGET IN AN OBJECT

(75) Inventors: Julius S. Cohen, Eindhoven (NL); Christine M. Thomas, Paris (FR)

(73) Assignee: Koninklijke Philips Electronics, N.V., Eindhoven (NL)

( * ) Notice: Subject to any disclaimer, the term of this patent is extended or adjusted under 35 U.S.C. 154(b) by 0 days.

(21) Appl. No.: 10/498,951

(22) PCT Filed: Dec. 18, 2002

(86) PCT No.: PCT/IB02/05625

§ 371 (c)(1),
(2), (4) Date: Jun. 16, 2004

(87) PCT Pub. No.: WO03/054577

PCT Pub. Date: Jul. 3, 2003

(65) Prior Publication Data

US 2005/0078788 A1 Apr. 14, 2005

(30) Foreign Application Priority Data

Dec. 21, 2001 (EP) .................................. 01403352

(51) Int. Cl.
*A61B 6/00* (2006.01)

(52) U.S. Cl. ............................ 378/19; 378/21; 378/62

(58) Field of Classification Search .................. 378/19, 378/21, 23, 24, 25, 26, 62, 64, 65, 207
See application file for complete search history.

(56) References Cited

U.S. PATENT DOCUMENTS 5,483,333 A * 1/1996 Dancer .................... 356/152.1
2005/0078788 A1 * 4/2005 Cohen et al. ................. 378/62

* cited by examiner

*Primary Examiner*—David V. Bruce
*Assistant Examiner*—Courtney Thomas

(57) ABSTRACT

A method for localizing a target (e.g., a tumor) in an object (e.g. human tissue) by scanning the object with an X-ray beam. The X-ray beam is translated and simultaneously rotated during the scan, the translatory and rotational movements being connected in such a way that the shadow image of the target is kept on the surface of a detector during the scan. In this way it is possible to measure the translation d of that image during the scan. From the translation in combination with the translation D and the rotation during the scan, the height of the target 2 above the detector surface 10 may be calculated. In this way only one scan is needed.

11 Claims, 3 Drawing Sheets

METHOD FOR LOCALIZING A TARGET IN AN OBJECT

Figure 1:
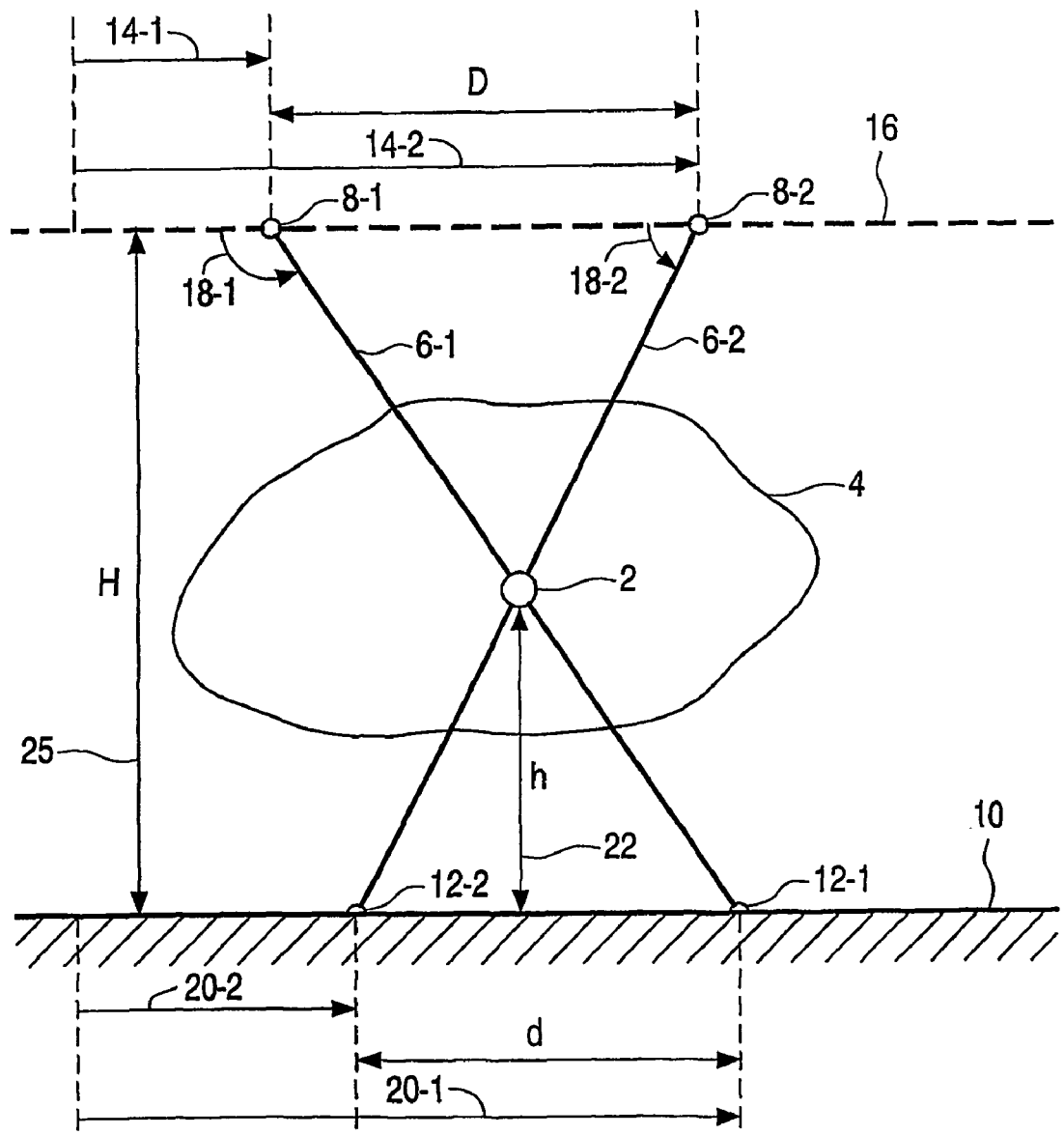

The invention relates to a method for localising a target in an object, comprising the steps of:
generating a fan shaped X-ray beam by means of an X-ray source;
scanning the fan shaped X-ray beam over the object thus projecting on the surface of an X-ray detector a shadow image of the object and of the target in it;
recording the orientation of the X-ray beam and the translatory position at at least two of its translatory positions during the scan and of the positions of the shadow image of the target on the surface of the detector;
calculating the position of the target with respect to the surface of the detector from the translation positions of the X-ray beam, its corresponding orientations and the corresponding positions of the shadow image of the target.

A method of this kind is known from the U.S. Pat. No. 5,483,333. This known method is directed to localising a medical target in an object like the body of a patient to be treated. In this method the X-ray beam is scanned twice over the part of interest of the body. During the first scan a shadow image of the object (i.e. the relevant body part) and the target in it is projected on an X-ray detector. During the second scan the position and the orientation of the X-ray beam is different from the position and orientation of that beam during the first scan. Also during the second scan a shadow image of the object and the target in it is projected on the X-ray detector, in such a way that the positions of the target on the detector are mutually different. In this way the height of the target above the detector surface can be calculated from the distance between the two shadow images of the target if both positions of the X-ray beam as well as both orientations are known.

The known method involves at least two scans of the object with a fan beam which is formed by a collimator in front of the x-ray focus of an X-ray source. In a first scan the fan beam is at a first inclination and the fan beam is scanned over the object by translating the x-ray source and the x-ray detector. During this scan it is detected at which detector elements the fan beam is first and last intercepted. Subsequently the translation of the x-ray source and x-ray detector is repeated at a different inclination. So in this known method two complete scans must be executed over the part of interest of the body to be examined. This means that an X-ray dose corresponding to two complete scans is received by that body part, which is a disadvantage of this known method.

The invention has for its object to provide a method for localising a target in an object using X-rays in which the radiation dose is lower than in the known method.

To this end the method according to the invention is characterised in that it comprises the step of translating and simultaneously rotating the X-ray beam during the scan of the X-ray beam, the translatory and rotational movements being connected in such a way that the shadow image of the target is kept on the surface of the detector during the scan. By applying this method step the shadow image of the target is kept on the detector during the scan. In this way it is possible to measure the displacement of that image during the scan, from which displacement in combination with the translation and the rotation during the scan the height of the target above the detector surface can be calculated. In this way only one scan is needed.

It is remarked that in said US-patent it is described that the x-ray source can be displaced and the orientation of the fan beam can be varied. However, in this known method the rotation of the X-ray source is used for adjusting the inclination before the translatory movement. It cannot be derived from this document that the translation and the rotation are performed simultaneously. So the X-ray beam still needs to be scanned twice over the object by translating the x-ray source for two orientations.

In a first embodiment of the method according to the invention
the orientation of the X-ray beam is varied from an initial orientation to a final orientation;
for the initial orientation an initial position of the shadow image on the detector surface is calculated;
for the final orientation a final position of the shadow image on the detector surface is calculated;
the position of the target is calculated from the initial position of the shadow image on the detector surface, and its final position.

It is possible that the shadow image of the target is automatically detected or indicated by a practitioner on a display. In such cases it is possible that the shadow image of the target is kept on the same position on the detector during the scan and that the orientation of the X-ray beam is controlled in such a way that the image position is constant. In this first embodiment however, there is no need for such (complicated) control, but it is sufficient that the shadow image of the target is kept on the detector during the scan. If the detector surface is sufficiently large, there is no need for any complicated control.

In a second embodiment of the method according to the invention
the orientation of the X-ray beam is varied at an angular rate of change;
the speed of the shadow image on the surface of the detector is calculated;
the position of the target is calculated from the angular rate of change of the orientation of the X-ray beam and the speed of the shadow image. In the latter embodiment the magnitude of the scan is not defined between two previously determined positions of the shadow image of the target, but during the scan the speed of that image is measured and it is calculated (f.i. on the basis of the required precision in the position of the target) whether the scan can be terminated. In this way no excess radiation dose is received by the object tissue.

In a third embodiment of the method according to the invention the X-ray beam initially is translated only until the shadow image of the target appears on the surface of the X-ray detector, and is subsequently translated and simultaneously rotated during the further scan of the X-ray beam, the translatory and rotational movements being connected in such a way that the shadow image of the target is kept on the surface of the detector during the scan. It is possible that during a scan in which the rotational movement of the beam is coupled with the translational movement, only a limited part of the object is scanned by the beam, thus missing the target. In such case a second scan would be needed, thus providing an additional X-ray dose to the object. By initially scanning the object with a fan shaped X-ray beam in a fixed orientation all object tissue is scanned until the target is found. After that the actual scan (i.e. translation coupled to rotation) may start, thus avoiding unnecessary X-ray dose by the object tissue.

The invention also relates to a computer programme. The computer programme concerns operating software that is used to control the operation of an X-ray examination apparatus. When the computer programme according to the invention is loaded in the working memory of a processor which controls the X-ray examination apparatus, then the X-ray examination apparatus is able to carry out the method of the invention.

Figure 2A:
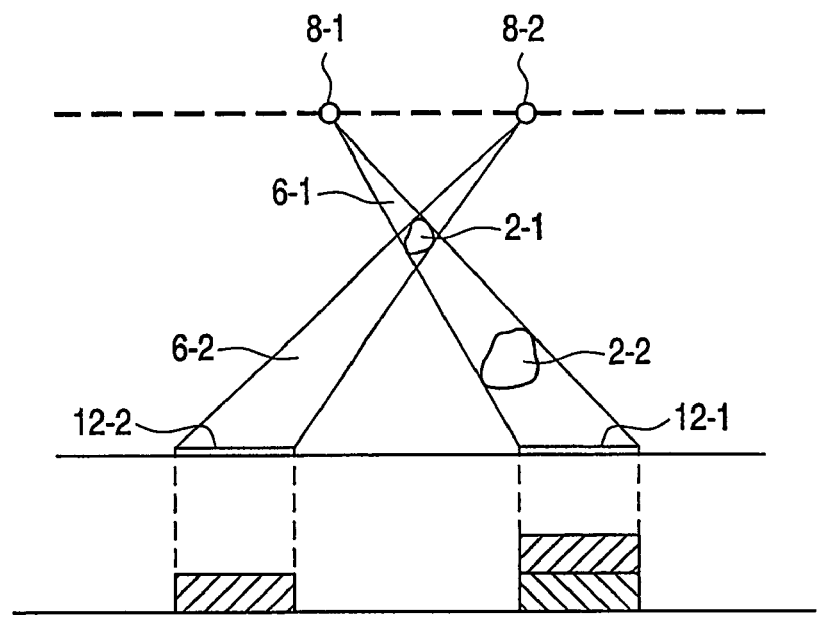
Figure 2B:
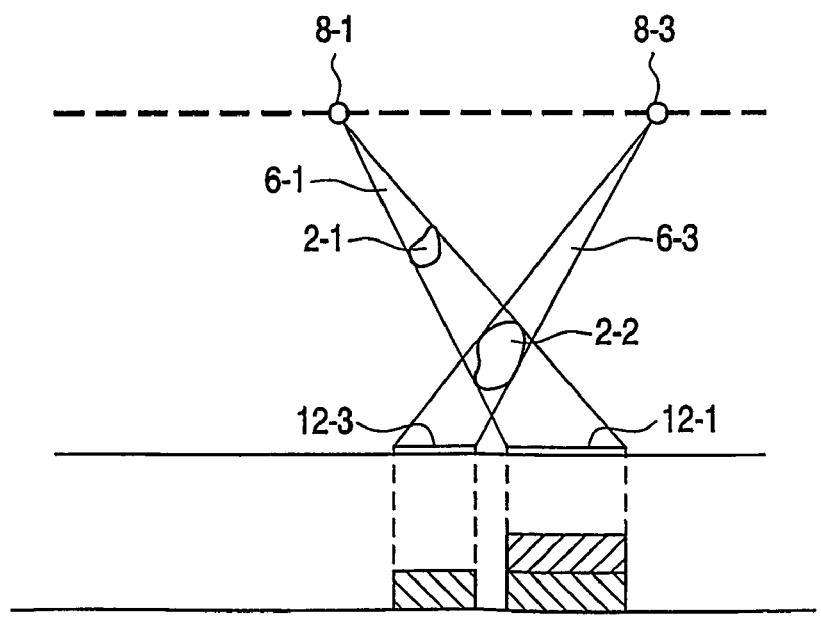
Figure 3:
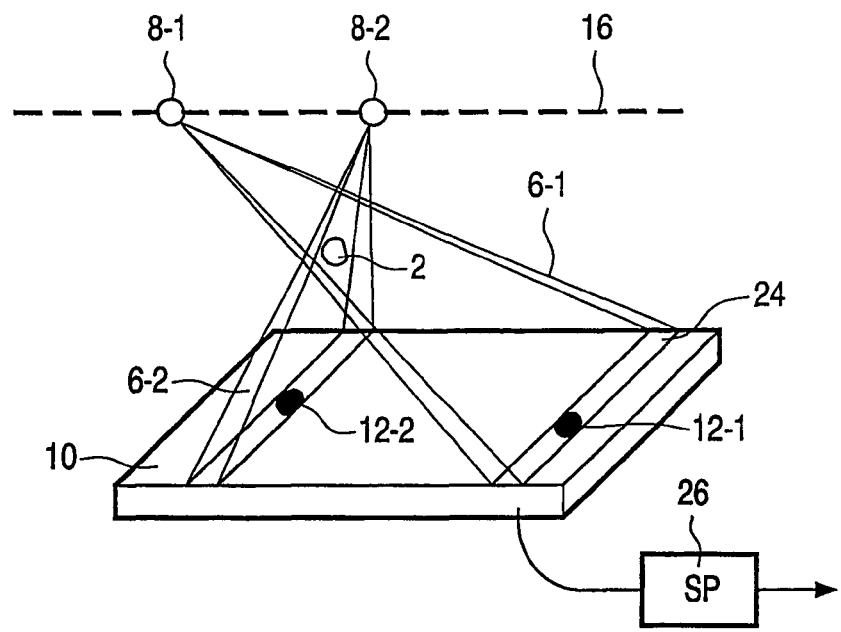
Figure 4:
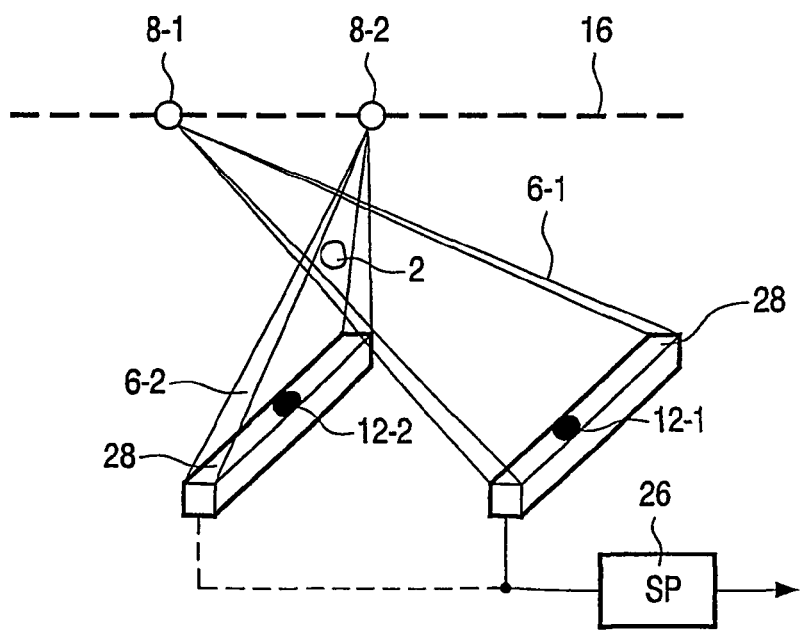

The invention will be now described in more detail with reference to the drawings. In these drawings:

FIG. 1: illustrates in a schematic drawing the general way of calculating the position of a target with respect to the surface of a detector;

FIGS. 2a and 2b: explain the general way of distinguishing between two targets in one object;

FIG. 3: illustrates a first embodiment of the invention using a first position sensitive X-ray detector;

FIG. 4: illustrates a second embodiment of the invention using a second position sensitive X-ray detector.

FIG. 1 shows a schematic drawing illustrating the general way of calculating the position of a target with respect to the surface of a detector by means of a scanning movement of the illuminating X-ray source. An object 4 to be examined containing a target 2 to be located is positioned in front of the surface of an X-ray detector 10. An X-ray source, generally indicated by reference 8, performs a scanning movement along a line 16 from a first position 14-1 (source 8-1) to a second position 14-2 (source 8-2) with respect to an arbitrary reference position. During the scanning movement the fan shaped X-ray beam 6 from the X-ray source 8 is kept directed towards the detector surface 10. The orientation of the source in position 14-1 is referenced to as 18-1 and the orientation of the source in position 14-2 is referenced to as 18-2. The X-ray beam projects a shadow image of the target 2 on the detector surface, in the first source position image 12-1 having a position 20-1 is projected and in the second source position image 12-2 having a position 12-2 is projected. The position of the target with respect to the detector surface 10 is indicated by means of line 22, having a value h. The distance from the scan path 16 to the detector surface 10 is indicated by means of line 25, having a value H. Assuming the difference of source positions 14-1 and 142 to be D and the difference of image positions 20-1 and 20-2 to be d, the position h can be expressed as a function of H, D and d as follows. From similarity of the triangles (8-1, 8-2, 2) and (12-1, 12-2, 2) it can be seen that $D/d=(H-h)/h$, from which it follows that $h=(Hd)/(D+d)$.

In the above explanation it is assumed that line 16 is parallel to surface 10. It is, however, possible that line 16 is not parallel to surface 10; in that case the calculation becomes somewhat more complicated but not fundamental impossible provided the starting and end positions 8-1 and 8-2 of the source 8 are known.

A further explanation of the invention is provided by FIGS. 2a and 2b.

The object, like in the prior art, e.g. a woman's breast containing a tumour as a target 2, is irradiated with X-rays from several source positions such as 8-1, 8-2 and 8-3 and at several orientations of the fan beam relative to the detector surface 10. At a first time instant $t_1$ a narrow fan-beam is used from position 8-1 at a first orientation to form a shadow at position 12-1 on the detector surface 10 and the signal supplied by the X-ray detector shows a portion of low X-ray intensity for the pixels corresponding to position 12-1 on which the shadow of the target 2-1 is thrown. Note that a small target 2-1 closer to the X-ray source at position 8-1 projects the same shadow and thus the same signal as a larger target 2-2 further away from the X-ray source. As the X-ray source is moved toward position 8-2 at a second orientation, the X-ray fan beam 6 scans over the object containing the targets and the shadows of the respective targets translate over the detector surface 10. When the X-ray source has arrived at position 8-2, the shadow of target 2-1 has travelled to position 12-2 and the shadow of target 2-2 has travelled outside of the fan beam 6. The detector signal at times $t_1$ and $t_2$ are schematically shown below the detector surface 10. At a third position 8-3 the shadow of target 2-2 has travelled to position 12-3. The detector signal at time $t_2$ is also shown schematically. From the translations of the shadows of each target both target positions can be determined from the expression for the position h shown above and the translation of the X-ray source from 8-1 to 8-2. The detector signal at times $t_1$ and $t_3$ are also schematically shown.

The method notably achieves that the target 2 can be maintained in the fan beam 6 as the scan beam scans over the object 4 to be investigated, such as a woman's breast. This enables as discussed above to determine the position of the target, such as a tumour in the breast tissue, with respect to the X-ray detector, independently of the (unknown) actual size of the target 2.

According to a slightly alternative implementation of the invention, the X-ray source 8 is translated at a predetermined, preferably constant velocity while the orientation of the fan beam 6 changes and from the changing signal supplied by the x-ray detector as the fan beam scans over de detection area, the translation speeds of the shadows of targets 2-1 and 2-2 are measured. From the measured speeds of the shadows, the velocity of the X-ray source and the time lapsed, the translation of the X-ray source and of the shadows on the detector surface can be simply calculated. Then, the targets 2-1 and 2-2 can be localised on the basis of the above derived expression for the position h. This embodiment may be easily incorporated in a conventional X-ray examination system in which the stand is moved by a motor which can be driven at a preset constant speed.

Although the invention relies on the same trigonometric principle as the method known from document D1, the required X-ray dose is reduced to about half the dose for according to the prior art as disclosed in document D1 the breast is exposed twice with an X-ray dose that must be sufficient to image the interior of the breast. According to the invention it is sufficient to scan fan-beam 6 only once over the breast 4 to localise all tumours (targets), which requires only the dose for a single X-ray exposure. Moreover, for the localisation of only a few targets, only a limited scan of the fan beam over the breast may be sufficient. For example, in order to resolve the targets 2-1 and 2-2 in FIG. 2, the fan-beam 6 needs to be scanned over the breast 4 only until the shadows of the respective targets 2-1 and 2-2 have moved apart over about the size of the shadows, which is far less than the size of the detection area Similarly, scanning may be limited until the different speeds of the shadows over the detection area have been established.

Several ways for adjusting the orientation of the fan beam 6 are available. For example, the X-ray tube 8 may be tilted on its support, or an X-ray tube with a movable focus spot may be used or an X-ray tube with a plurality of focus spots may be employed.

FIG. 3 shows a perspective view of a first embodiment of the invention. In the detector surface 10 an array of X-ray detector elements is positioned. In this embodiment the X-ray detector may be stationary. Such an X-ray detector array derives an electronic signal from the X-ray intensities in the fan beam 6. Usually, such detector has 1000×1000 detector elements which can be read-out at a frame rate of 60 fps (frames/second). The fan beam 6 irradiates a narrow strip of pixels 24 in the X-ray detector surface 10. The X-ray intensities, i.e. the pixel-values, in the strip 24 of pixels represent the X-ray intensities in the fan beam 6 which are lower if they are attenuated by the target. The irradiated strip 24 of pixels translates over the detector surface 10 as the fan beam 6 is scanned over the breast (not shown) and the shadow image 12 of the target 2 (tumour) is translated over the detector surface. Such detector can be read out at a very high frame rate e.g. 6000 strips per second if a strip of 10 pixels wide is used. The electronic signals representing the X-ray intensities at the successive read-out strips are fed into the signal processor (SP) which detects the pixels pertaining to the shadow of each target. These detected pixels represent the position of the shadow and as the fan beam 6 is scanned over the detector surface (and over the object), the signal processor 26 is able to follow the shadow image as it translates over the detector surface 10.

FIG. 4 shows a more simple (so less expensive) strip formed detector array 28. Preferably, the strip detector has a width of about 10 detector elements in the scan direction, but a linear detector array may also be used. The strip shaped detector 28 shown in FIG. 4 is translated similar to the translation of the x-ray source 8 along translation line 16. As the fan beam 6 is scanned over de detector surface, the strip detector 24 is also translated over the detector surface. Thus, the strip detector 24 tracks the shadow image of the tumours and as the fan beam scans over the detector surface and the strip detector moves through the detection area an electronic signal varying in time which is similar to the signal according to FIG. 3 is supplied to the signal processor.

In the embodiments of FIG. 3 as well as FIG. 4 the signal processor can be arranged to automatically detect the occurrence and vanishing of the shadow image of a target. Notably, upon detection of vanishing of the shadow image further scanning of the fan beam (and thus additional x-ray exposure of the patient's body) is stopped. The orientation of the fan beam 6 is preferably varied in such a way that a particular shadow of a very suspected tumour is kept in view. To that end the operator may manually control the orientation of the fan beam 6, based upon an image presented by of the irradiated strip.

The signal processor 26 may also be programmed to automatically detect suspected tumours as a target, e.g. based upon irregularly shaped shadow images which are indicative for cancer. In another implementation of the invention, a contrast agent may be administered to the patient and the time variation of the x-ray absorption, represented as varying brightness values in the ensuing shadow images may be monitored by the signal processor 26. In particular, shadow images in which the additional x-ray absorption due to the contrast agent has a strong onset and disappears rapidly are indicative for areas with many but leaky blood vessels as will appear in cancer regions.

In a preferred embodiment of the invention the fan beam 6 in a first stage is scanned over the object 4 while having a first fixed orientation until the shadow of the target is detected. Subsequently, the orientation of the beam is varied so as to keep the shadow image of the target in the fan beam as the fan beam continues to scan along line 16 over the object 4. This implementation is in particular advantageous because the object 4 may be searched for the target that is subsequently located without the need for a further scan, so additional x-ray exposure is avoided.

The invention claimed is:

1. A method for localizing a target in an object, comprising the acts of:

generating a fan shaped X-ray beam by means of an X-ray source;

scanning the fan shaped X-ray beam over the object thus projecting on the surface of an X-ray detector a shadow image of the object and of the target in it;

translating and simultaneously rotating the X-ray beam during the scan of the X-ray beam, the translatory and rotational movements being connected in such a way that the shadow image of the target is kept on the surface of the detector during the scan;

recording the orientation and the translatory position of the X-ray beam at at least two of its translatory positions during the scan and of the positions of the shadow image of the target on the surface of the detector;

calculating the position of the target with respect to the surface of the detector from the translation positions of the X-ray beam, its corresponding orientations and the corresponding positions of the shadow image of the target.

2. The method as claimed in claim 1, wherein
the orientation of the X-ray beam is varied from an initial orientation to a final orientation;
for the initial orientation an initial position of the shadow image on the detector surface is calculated;
for the final orientation a final position of the shadow image on the detector surface is calculated;
the position of the target is calculated from the initial position of the shadow image on the detector surface, its final position, its initial position and its final position.

3. The method as claimed in claim 1, wherein
the orientation of the X-ray beam is varied at an angular rate of change;
the speed of the shadow image on the surface of the detector is calculated;
the position of the target is calculated from the angular rate of change of the orientation of the X-ray beam and the speed of the shadow image.

4. The method as claimed in claim 1, wherein the X-ray beam initially is translated only until the shadow image of the target appears on the surface of the X-ray detector, and is subsequently translated and simultaneously rotated during the further scan of the X-ray beam, the translatory and rotational movements being connected in such a way that the shadow image of the target is kept on the surface of the detector during the scan.

5. A computer readable medium including a computer program comprising a set of instructions for control of an x-ray examination apparatus, said set of instructions including
an instruction to generate a fan shaped X-ray beam by means of an X-ray source;
an instruction to scan the fan shaped X-ray beam over the object thus projecting on the surface of an X-ray detector a shadow image of the object and of the target in it;
an instruction to translate and simultaneously rotate the X-ray beam during the scan of the X-ray beam, the translatory and rotational movements being connected in such a way that the shadow image of the target is kept on the surface of the detector during the scan;
an instruction to record the orientation and the translatory position of the X-ray beam at at least two of its translatory positions during the scan and of the positions of the shadow image of the target on the surface of the detector; and an instruction to calculate the position of the target with respect to the surface of the detector from the translation positions of the X-ray beam, its corresponding orientations and the corresponding positions of the shadow image of the target.

6. A method for localizing a target in an object, comprising the acts of:

scanning an X-ray beam over the object to project on an X-ray detector a shadow image of the object and of the target; and translating and simultaneously rotating the X-ray beam during the scanning act, the translatory and rotational movements being connected in such a way that the shadow image of the target is kept on the detector during the scan.

7. The method of claim 6, further comprising the acts of:

recording an orientation and a translatory position of the X-ray beam at at least two of translatory positions during the scanning act and of the positions of the shadow image of the target on the detector; and calculating the position of the target with respect to the detector from the translation positions of the X-ray beam, its corresponding orientations and the corresponding positions of the shadow image of the target.

8. A system for localizing a target in an object, comprising:

means for scanning an X-ray beam over the object to project on an X-ray detector a shadow image of the object and of the target; and means for translating and simultaneously rotating the X-ray beam during the scanning act, the translatory and rotational movements being connected in such a way that the shadow image of the target is kept on the detector during the scan.

9. The system of claim 8, further comprising:

means for recording an orientation and a translatory position of the X-ray beam at at least two of translatory positions during the scanning act and of the positions of the shadow image of the target on the detector; and means for calculating the position of the target with respect to the detector from the translation positions of the X-ray beam, its corresponding orientations and the corresponding positions of the shadow image of the target.

10. A machine-readable medium containing one or more software programs which when executed control a system for localizing a target in an object, by implementing the acts of:

scanning an X-ray beam over the object to project on an X-ray detector a shadow image of the object and of the target; and translating and simultaneously rotating the X-ray beam during the scanning act, the translatory and rotational movements being connected in such a way that the shadow image of the target is kept on the detector during the scan.

11. The machine-readable medium of claim 10 which when executed further implementing the acts of:

recording an orientation and a translatory position of the X-ray beam at at least two of translatory positions during the scanning act and of the positions of the shadow image of the target on the detector; and calculating the position of the target with respect to the detector from the translation positions of the X-ray beam, its corresponding orientations and the corresponding positions of the shadow image of the target.

* * * * *